(12) United States Patent
Hill

(10) Patent No.: US 11,918,549 B2
(45) Date of Patent: Mar. 5, 2024

(54) SYSTEM AND METHOD FOR WOUND TREATMENT AND IRRIGATION

(71) Applicant: AZ SOLUTIONS LLC, Bloomfield Hills, MI (US)

(72) Inventor: Derek Hill, Bloomfield Hills, MI (US)

(73) Assignee: AZ SOLUTIONS LLC, Bloomfield Hills, MI (US)

( * ) Notice: Subject to any disclaimer, the term of this patent is extended or adjusted under 35 U.S.C. 154(b) by 796 days.

(21) Appl. No.: 16/641,749

(22) PCT Filed: Aug. 27, 2018

(86) PCT No.: PCT/US2018/048149
§ 371 (c)(1),
(2) Date: Feb. 25, 2020

(87) PCT Pub. No.: WO2019/040939
PCT Pub. Date: Feb. 28, 2019

(65) Prior Publication Data
US 2020/0390808 A1    Dec. 17, 2020

Related U.S. Application Data

(63) Continuation-in-part of application No. 15/686,612, filed on Aug. 25, 2017, now Pat. No. 10,960,129,
(Continued)

(51) Int. Cl.
*A61K 31/155* (2006.01)
*A61K 31/4425* (2006.01)
(Continued)

(52) U.S. Cl.
CPC ........ *A61K 31/155* (2013.01); *A61K 31/4425* (2013.01); *A61K 33/30* (2013.01);
(Continued)

(58) Field of Classification Search
CPC .. A61K 33/38; A61K 31/155; A61K 31/4425; A61K 33/30; A61K 33/34;
(Continued)

(56) References Cited

U.S. PATENT DOCUMENTS 4,540,403 A    9/1985  Theeuwes
4,786,279 A   11/1988  Wilkinson et al.
(Continued)

FOREIGN PATENT DOCUMENTS

CN    1248155 A    3/2000
CN  104826114 A    8/2015
(Continued)

OTHER PUBLICATIONS

Japanese Office Action dated Sep. 8, 2022 for JP Application No. 20205322868. English translation provided.
(Continued)

*Primary Examiner* — Susan S Su
*Assistant Examiner* — Eric Rassavong
(74) *Attorney, Agent, or Firm* — BROOKS KUSHMAN P.C.

(57) ABSTRACT

A wound irrigation system includes a first fluid including an ion rich compound having free available ions; and a second fluid including an oxidation-reduction potential increasing compound, the second fluid housed separately from the first fluid. Mixing the first and second fluids in a charging area forms an ionically charged fluid with an oxidation-reduction potential higher than a wound site oxidation-potential. The ionically charged fluid increases antimicrobial activity of the wound upon application.

20 Claims, 5 Drawing Sheets

Related U.S. Application Data which is a continuation-in-part of application No. 15/686,617, filed on Aug. 25, 2017, now abandoned.

(60) Provisional application No. 62/660,676, filed on Apr. 20, 2018.

(51) Int. Cl.
| | |
|---|---|
| A61K 33/30 | (2006.01) |
| A61K 33/34 | (2006.01) |
| A61K 33/38 | (2006.01) |
| A61K 45/06 | (2006.01) |
| A61M 1/00 | (2006.01) |
| A61M 3/02 | (2006.01) |

(52) U.S. Cl.
 CPC ............. *A61K 33/34* (2013.01); *A61K 33/38* (2013.01); *A61M 3/0241* (2013.01); *A61M 3/0258* (2013.01); *A61M 3/0262* (2013.01); *A61K 45/06* (2013.01); *A61M 1/77* (2021.05); *A61M 3/0245* (2013.01)

(58) Field of Classification Search
 CPC ........... A61K 45/06; A61M 1/77; A61M 1/92; A61M 3/0245; A61M 3/005; A61M 3/0241; A61M 3/0258; A61M 3/0262; A61M 3/0279; A61M 3/0287; A61M 35/003; A61M 3/00
 See application file for complete search history.

(56) References Cited

U.S. PATENT DOCUMENTS

| | | | |
|---|---|---|---|
| 5,059,187 A | 10/1991 | Sperry et al. | |
| 5,125,837 A | 6/1992 | Warrin et al. | |
| 5,152,461 A | 10/1992 | Proctor | |
| 5,227,168 A | 7/1993 | Chvapil et al. | |
| 5,411,176 A | 5/1995 | Favre | |
| 5,753,217 A | 5/1998 | Christopfel | |
| 5,830,197 A | 11/1998 | Rucinski | |
| 5,908,865 A | 6/1999 | Doe et al. | |
| 6,283,936 B1 | 9/2001 | Tavger | |
| 6,319,243 B1* | 11/2001 | Becker | B32B 27/08 |
| | | | 206/568 |
| 6,409,992 B1* | 6/2002 | Kleinberg | A61K 8/20 |
| | | | 424/614 |
| 6,423,300 B1 | 6/2002 | Kleinberg et al. | |
| 6,558,710 B1 | 5/2003 | Godfrey | |
| 6,635,035 B1 | 10/2003 | Marasco | |
| 6,929,790 B2 | 8/2005 | Kleinberg et al. | |
| 6,946,142 B2 | 9/2005 | Chang et al. | |
| 7,959,617 B2 | 6/2011 | Rucinski | |
| 8,562,907 B2* | 10/2013 | Green | A01N 59/00 |
| | | | 134/99.1 |
| 9,044,466 B2 | 6/2015 | Cohen et al. | |
| 9,433,711 B2 | 9/2016 | Pratt et al. | |
| 9,549,878 B2 | 1/2017 | Le Ouay et al. | |
| 9,556,471 B2* | 1/2017 | LeJuene | C12Q 1/37 |
| 10,137,467 B2 | 11/2018 | Alluigi | |
| 2002/0068913 A1 | 6/2002 | Fleischmann | |
| 2002/0074347 A1* | 6/2002 | Murray | B65D 81/3283 |
| | | | 222/129 |
| 2004/0063600 A1 | 4/2004 | Williams et al. | |
| 2004/0141961 A1 | 7/2004 | Demeester et al. | |
| 2005/0035153 A1 | 2/2005 | Brown | |
| 2005/0192546 A1 | 9/2005 | Griego et al. | |
| 2006/0155260 A1 | 7/2006 | Blott et al. | |
| 2007/0029275 A1* | 2/2007 | Hantman | B65D 81/3288 |
| | | | 222/129 |
| 2007/0141128 A1 | 6/2007 | Blott | |
| 2007/0225662 A1* | 9/2007 | Rucinski | A61M 3/0262 |
| | | | 604/290 |
| 2007/0225663 A1 | 9/2007 | Watt et al. | |
| 2007/0237810 A1 | 10/2007 | Wellinghoff | |
| 2008/0113956 A1 | 5/2008 | Fridovich et al. | |
| 2011/0054283 A1 | 3/2011 | Shuler | |
| 2011/0097372 A1 | 4/2011 | Rucinski | |
| 2012/0035559 A1 | 2/2012 | Rucinski | |
| 2012/0302973 A1 | 11/2012 | Locke | |
| 2013/0164358 A1 | 6/2013 | Cohen et al. | |
| 2013/0165821 A1* | 6/2013 | Freedman | A61M 1/85 |
| | | | 604/20 |
| 2013/0178785 A1 | 7/2013 | Papay et al. | |
| 2013/0270490 A1 | 10/2013 | De La Vega | |
| 2014/0213990 A1 | 7/2014 | Gorinshteyn | |
| 2014/0263448 A1* | 9/2014 | Erskine-Smith | B65D 35/22 |
| | | | 222/143 |
| 2014/0276288 A1 | 9/2014 | Randolph et al. | |
| 2014/0364818 A1 | 12/2014 | Vogt | |
| 2015/0216765 A1 | 8/2015 | Le Ouay | |
| 2015/0232260 A1 | 8/2015 | Dann et al. | |
| 2015/0258257 A1 | 9/2015 | Kidman | |
| 2015/0298149 A1* | 10/2015 | Alluigi | B05B 11/3057 |
| | | | 222/135 |
| 2016/0000088 A1 | 1/2016 | Nakamura et al. | |
| 2016/0136350 A1 | 5/2016 | Yoo | |
| 2016/0235692 A1 | 8/2016 | Rucinski | |
| 2016/0279138 A1 | 9/2016 | Surber et al. | |
| 2016/0325028 A1 | 11/2016 | Locke et al. | |
| 2017/0028144 A1 | 2/2017 | Flickinger | |
| 2017/0080219 A1* | 3/2017 | Balsamo | A61M 3/0204 |
| 2017/0100338 A1 | 4/2017 | Awad et al. | |
| 2017/0121098 A1 | 5/2017 | Kaiser et al. | |
| 2017/0216852 A1 | 8/2017 | Gopalan et al. | |
| 2017/0239455 A1* | 8/2017 | Richards | B05B 11/3081 |
| 2019/0322442 A1 | 10/2019 | Thomsen | |
| 2020/0039732 A1 | 2/2020 | Ditto et al. | |
| 2020/0390808 A1 | 12/2020 | Hill | |
| 2021/0252048 A1 | 8/2021 | Hill | |

FOREIGN PATENT DOCUMENTS

| | | | | |
|---|---|---|---|---|
| CN | 106687218 A | | 5/2017 | |
| JP | 2002524212 A | | 8/2002 | |
| JP | 2015147766 A | | 8/2015 | |
| WO | WO-2005030297 A1 * | | 4/2005 | .......... A61M 3/0262 |
| WO | WO-2005046761 A1 * | | 5/2005 | ....... A61F 13/00063 |
| WO | 2011/130246 A2 | | 10/2011 | |

OTHER PUBLICATIONS

First Indian Office Action dated Sep. 9, 2021 for Indian Application No. 202017012635, received in related application.

Notice of Allowance received in corresponding U.S. Appl. No. 15/686,612 dated Dec. 10, 2020.

International Search Report for PCT/US18/48149, dated Oct. 5, 2018.

C. Wu et al., "Zinc as an agent for the prevention of biofilm formation by pathogenic bacteria," Journal of Applied Microbiology, vol. 115, pp. 30-40, 2013.

S.C. Fu, et al., "Development of vitamin C irrigation saline to promote graft healing in anterior cruciate ligament reconstruction," Journal of Orthopaedic Translation, vol. 1, pp. 67-77, 2013.

Z. Tang, et al., "Design and characterizations of novel biodegradable Zn—Cu—Mg alloys for potential biodegradable implants," Materials and Design, vol. 117, pp. 84-94, 2017.

J. Niu, et al., "Research on a Zn—Cu alloy as a biodegradable material for potential vascular stents application," Materials Science and Engineering C., vol. 69, pp. 407-413, 2016.

L.K. Hung, et al., Local Vitamin-C Injection Reduced Tendon Adhesion in a Chicken Model of Flexor Digitorum Profundus Tendon Inquiry, The Journal of Bone and Joint Surgery, vol. 95:e41, pp. 1-7, 2013.

"Pneumonia," Wikipedia, 2009, <https://en.wikipedia.org/wiki/Pneumonia>] para. 2, [retrieved from the internet on Jun. 29, 2022].

International Search Report, dated Jul. 28, 2022, for International Application No. PCT/US22/27648, received in a related application.

(56) References Cited

OTHER PUBLICATIONS

International Search Report for PCT/US2018/048149, dated Apr. 20, 2021.
European Office Action dated Mar. 22, 2023 which issued in related EP Application No. 18 847 925.7. 6 pages.
NPL_First Office Action dated Sep. 4, 2023 for Chinese Application No. 201880055296.3 which issued in related application. 10 pages.
Australian Office Action dated Jun. 30, 2023 which issued in related Australian Application No. 2018321929. 3 pages.
NPL_International Preliminary Report on Patentability dated Oct. 24, 2023 for PCT/US2022/027648, which issued in a related application. 6 pages.

* cited by examiner

SYSTEM AND METHOD FOR WOUND TREATMENT AND IRRIGATION

CROSS-REFERENCE TO RELATED APPLICATIONS

This application is the U.S. National Phase of Per Application No. PCT/US2018/048149 filed Aug. 27, 2018 which claims priority to U.S. application Ser. No. 15/686,612, filed Aug. 25, 2017, (now U.S. Pat. No. 10,960,129, issued Mar. 30, 2021), U.S. application Ser. No. 15/686,617, filed Aug. 25, 2017, (now abandoned), and U.S. provisional application No. 62/660,676, filed Apr. 20, 2018, the disclosures of which are hereby incorporated in their entirety by reference herein.

TECHNICAL FIELD

This disclosure relates to a system, method, and composition for wound and surgical irrigation, and more particularly ionically charged chemical compositions to help cure, control, or prevent infections.

BACKGROUND

Surgical sites, tissues, body fluids, joints, prosthetic joints, electrical, metal or synthetic implants, peritoneum, organs, body cavities, tissues, abscesses, and wounds, such as traumatic, thermal or chronically occurring wounds, such as diabetic or vascular foot or leg ulcers, can become inoculated during surgery or infected with bacteria or other infectious organisms which can spread and cause damage to surrounding tissue. These may hereinafter be referred to as skin or wound or any of the above listed areas interchangeably. In addition, implanted medical devices can also be inoculated or infected during or after implantation, including defibrillators, hip and knee prostheses, breast implants, spine instruments and disc replacements, pacemakers, spinal cord stimulators, coronary and vascular stents, ear tubes, artificial eye lenses and others. Wounds and surgical sites are prone to infection in humans, such as in medical settings, but also in animals, such as in veterinary settings. Prophylaxis to prevent and/or cure infections can be provided by eradicating bacterial colonization or contamination in the body cavity, organs, tissues, skin site, wound, or surgical site. Further, prevention of infection, inoculation or colonization of wounds, surgical sites, or chronically occurring wounds can be provided by a lasting antimicrobial activity in a nontoxic irrigant which offers persistent antimicrobial activity. This can be accomplished if the irrigant is allowed to remain in or around the wound or above mentioned areas, eliciting persistent antimicrobial activity.

SUMMARY

Disclosed herein are implementations of aspects, features, elements, implementations, and embodiments of irrigating a patient's wounds, surgical sites, body cavities, organs, tissues or skin.

According to an embodiment, a method for irrigating a wound includes keeping a first fluid separate from a second fluid in a container, the first fluid including an ion rich compound having free available ions, and the second fluid including an oxidation-reduction potential increasing compound, mixing the first fluid with the second fluid in a fluid charging portion of the container to form an ionically charged or ionized or activated fluid, hereinafter referred to as "charged" or "ionically charged," and applying the ionically charged fluid to the wound to increase antimicrobial activity at the wound.

According to one or more embodiments, the first fluid may include a source of zinc ions, copper ions, silver ions, or a mixture thereof, and the second fluid includes a source of chlorite ions. In one or more embodiments, the first fluid and/or second fluid may further include an antibiotic compound, an antiseptic compound, or both. In at least one embodiment, the method may further comprise keeping a third fluid having antiseptic and/or antibiotic properties separate from the first and second fluids, and mixing the third fluid in the fluid charging portion with the first and second fluids to form the ionically charged fluid. In some embodiments, the antiseptic may include chlorhexidine gluconate, cetylpyridinum chloride, or a mixture thereof. In certain embodiments, applying the ionically charged fluid may include delivering the ionically charged fluid to the wound via an irrigator sleeve configured to at least partially enclose the wound. In at least one embodiment, mixing the first fluid and the second fluid may include actuating a release to combine the first and second fluids in the fluid charging portion. Further, actuating the release may include creating a vacuum in the container to draw the first and second fluids into the fluid charging portion.

According to another embodiment, an infection suppression method includes separately housing an ion rich fluid having free available ions and an oxidation-reduction potential increasing fluid; and suppressing infectious activity by applying a mixture of the ion-rich fluid and oxidation-reduction potential increasing fluid at a potential infection site to increase an oxidation-reduction potential of the potential infection site and reduce bacterial proliferation.

According to one or more embodiments, the first fluid may include a source of zinc ions, copper ions, silver ions, or a mixture thereof. In at least one embodiment, the second fluid may include a source of chlorite ions. In some embodiments, applying the mixture may include delivering the ion-rich fluid and oxidation-reduction potential increasing fluid separately to the potential infection site to form a charged fluid at the potential infection site. In other embodiments, applying a mixture may include delivering the ion-rich fluid and oxidation-reduction potential increasing fluid to a charging portion to form the mixture, and releasing the mixture onto the potential infection site. In at least one embodiment, the mixture may further include an antiseptic fluid, an antibacterial fluid, a vitamin-rich fluid, a protein, or mixtures thereof.

According to an embodiment, a wound irrigation system includes a first fluid including an ion rich compound having free available ions; and a second fluid including an oxidation-reduction potential increasing compound, the second fluid housed separately from the first fluid. Mixing the first and second fluids in a charging area forms an ionically charged fluid with an oxidation-reduction potential higher than a wound site oxidation-reduction potential. The ionically charged fluid increases antimicrobial activity of the wound upon application.

According to one or more embodiments, the first fluid may include a source of zinc ions, copper ions, silver ions, or a mixture thereof, and the second fluid may include a source of chlorite ions. In at least one embodiment, the first fluid, the second fluid, or both, may include an antiseptic compound, antibiotic compound, a vitamin-rich compound, a protein, or a mixture thereof. In other embodiments, the wound irrigation system may further comprise a third fluid housed separate from the first and second fluids, and the third fluid may include an antiseptic compound, antibiotic compound, a vitamin-rich compound, a protein, or a mixture thereof, wherein mixing the first, second, and third fluids in a charging area forms the ionically charged fluid. In at least one embodiment, the antiseptic compound may include chlorhexidine gluconate, cetylpyridinium chloride, or a mixture thereof. In one or more embodiments embodiments, the vitamin-rich compound may include Vitamin A, Vitamin C, Vitamin D, Vitamin E, Vitamin $B_{1-6}$, Vitamin $B_{12}$, or mixtures thereof.

An aspect of the disclosed embodiments is a system for irrigating a patient's skin, wound, or tissues. The system includes a fluid container that includes a first compartment and a second compartment, the first compartment being adapted to retain a first fluid on a first side of a divider and the second compartment being adapted to retain a second fluid on a second side of the divider. The system also includes an irrigation sleeve adapted to cover a portion of the patient's skin. The system also includes a fluid charging portion adapted to receive a portion of the first fluid and a portion of the second fluid, wherein the portion of the first fluid reacts with the portion of the second fluid to form a charged compound in the fluid charging portion. The system also includes a compound delivery portion that extends at a first end of the compound delivery portion from the fluid charging portion, the compound delivery portion being adapted to deliver the charged compound from the fluid charging portion to the irrigation sleeve.

Another aspect of the disclosed embodiments is a method for irrigating a patient's skin, wound, or tissues. The method includes: retaining a first fluid on a first side of a divider; retaining a second fluid on a second side of a divider, the second side of the divider being disposed opposite the first side of the divider; covering a portion of the patient's skin with an irrigation sleeve; receiving a portion of the first fluid and a portion of the second fluid, wherein the portion of the first fluid reacts with the portion of the second fluid to form a charged compound; and delivering the charged compound from a fluid charging portion to the irrigation sleeve.

Another aspect of the disclosed embodiments is a system for irrigating a patient's skin, wound, or tissues. The system includes an irrigation sleeve adapted to cover a portion of the patient's skin, wound, or tissues. The system also includes a fluid charging portion adapted to receive a portion of a first fluid and a portion of a second fluid, wherein the portion of the first fluid reacts with the portion of the second fluid to form a charged compound in the fluid charging portion. The system also includes a compound delivery portion adapted to deliver the charged compound from the fluid charging portion to the irrigation sleeve while the charged compound is charged.

BRIEF DESCRIPTION OF THE DRAWINGS

The disclosure is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity.

DETAILED DESCRIPTION

Figure 1:
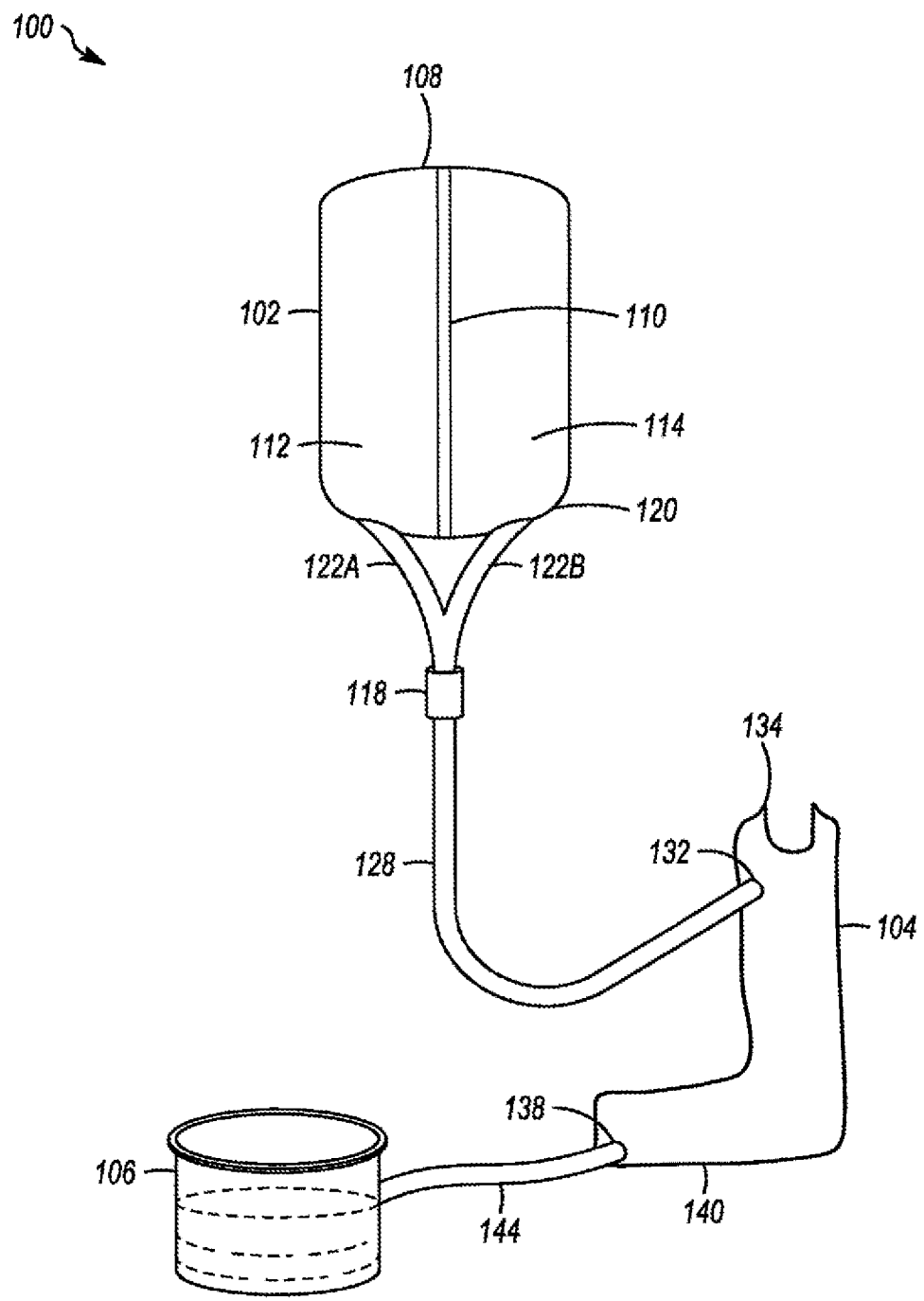
FIGS. 1 and 2 generally illustrate a wound and/or skin irrigation system according to the principles of the present disclosure.

As required, detailed embodiments of the present invention are disclosed herein; however, it is to be understood that the disclosed embodiments are merely examples of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention.

Surgical sites, body fluids, joints, tissues, organs, body cavities, abscesses, and acute or chronically occurring wounds may require irrigation to help prevent and/or cure infections caused by aerobic or anaerobic bacteria or other microorganisms. Although surgical sites, or wound sites, are discussed below, this is not intended to be limiting and includes open wounds, burn wounds, bodily fluids, traumatic wounds, chronically occurring wounds, graft sites (e.g., skin grafts), infections of any kind, such as, but not limited to, dermatological wounds or infections, tissue infections, and other infected areas of a human or animal body. Surgical wounds or chronically occurring wounds can become infected with bacteria or other infectious organisms, e.g., anaerobic bacteria, aerobic bacteria, gram positive bacteria, gram negative bacteria, viruses, prions, fungus, parasites, or other pathogens. Prophylaxis to prevent and/or solutions to cure infections can be provided by preventing inoculation or contamination. Further, prevention or treatment of infection, inoculation, or colonization of surgical wounds or chronically occurring wounds can be provided by a lasting antimicrobial activity in a wound irrigant which offers persistent antimicrobial activity. This can be accomplished if the irrigant is allowed to remain in or around the wound, eliciting persistent antimicrobial activity.

Metabolism and growth of bacteria, for example, in such wounds may increase when an oxidation-reduction potential ($E_h$) is decreased. The $E_h$ in such wound areas can decrease, for example, when oxygen in the wound area is decreased, through bacterial mechanisms, or in response to other changes in the characteristics of the wound area. Conversely, by increasing the $E_h$ in a wound area, metabolism and growth of bacteria may be decreased, which may prevent and/or cure an infection in a wound area. In certain instances, the metabolism and growth of the microorganisms may be prevented by increasing the oxidation-reduction (redox) potential (or $E_h$) of the wound site by irrigating the wound or infected area. Furthermore, irrigation may help eradicate and/or prevent the formation of biofilms at the wound site. Biofilms are a microbial resistance to host defenses and antibiotics, and preventing or eradicating their growth or production can eradicate or eliminate microorganism infection, inoculation, colonization or other pathology.

Increasing the $E_h$ in a wound area may include irrigating the wound area with one or more electron-rich or ion-rich compounds, such as a charged zinc compound having free available zinc ions and at least one $E_h$ raising component.

Accordingly, a system that charges a charged compound (or wound irrigant or charged fluid) and provides the charged compound to a wound area, e.g. a body cavity, joint, tissue, organ, wound or surgical site, and/or the patient's skin, hereinafter referred to interchangeably, is desirable.

According to one or more embodiments of the present disclosure, to increase the redox potential of a wound site, one or more electron-rich or ion-rich compounds, such as ionically charged chemical compositions (e.g., zinc, copper, or silver) having free available ions, and at least one redox potential raising component, may be used to irrigate the wound or tissue. Solutions suitable for irrigating wound sites and increasing the redox potential for infection prevention/control/curing include, but are not limited to, solutions forming $Zn^{2+}$, $Ag^+$ or $Cu^{2+}$ ions, or solutions with any combination of zinc, copper, and silver ions. In certain embodiments, the solutions include salts of a weak acid to provide the free available ions in the charged compound. In at least one embodiment, the weak acid is soluble in water. Examples of zinc compounds that form solutions with free available zinc ions include, but are not limited to, zinc chloride, zinc acetate, zinc lactate, zinc salicylate, zinc sulfate, zinc nitrate, zinc stearate, zinc gluconate, zinc ammonium sulfate, zinc chromate, zinc citrate, zinc dithionate, zinc fluorosilicate, zinc tartrate, zinc formate, zinc iodide, zinc phenol sulfonate, zinc succinate, zinc glycerophosphate, or other zinc halides. Examples of copper compounds that form solutions with free available copper ions include, but are not limited to copper acetate, copper formate, copper citrate, copper lactate, copper oxalate, copper propionate, copper benzoate, copper succinate, copper malonate, copper stearate, copper gluconate, copper ammonium sulfate, copper chromate, copper dithionate, copper fluorosilicate, copper tartrate, copper iodide, copper nitrate, copper phenol sulfonate, copper salicylate, copper sulfate, copper glycerophosphate, or other copper halides. Examples of silver compounds that form solutions with free available silver ions include, but are not limited to silver sulfate, silver oxide, silver acetate, silver nitrate, silver citrate, silver chloride, silver lactate, silver phosphate, silver stearate, silver thiocyanate, silver saccharinate, silver anthranilate, silver carbonate, or other silver halides. The solutions providing the ions, or mixed with such solution, may have preferred solubility for the specific ion selected, as well as provide an effective amount of ions without permitting the redox potential to fall to unwanted levels. Hereinafter, the wound irrigant formed by the combining the solutions may be referred to as a "charged wound irrigant," "charged fluid," "ionically charged fluid," or "charged compound." For example, to form zinc ions, $ZnCl_2$ and $NaClO_2$ may be used as two solutions to form the charged wound irrigant. The two solutions may be combined in a charging area to form a charged compound having free available ions and at least one redox-potential-raising component (e.g., the $NaClO_2$ is a source of chlorite ions to raise the redox potential while also interacting with the $ZnCl_2$).

In some embodiments, according to the principles of the present disclosure, an ion-rich or electron-rich compound suitable for treating such wound areas can be formed by combining a first fluid and a second fluid in a charging area. For example, in some embodiments, a system for irrigating a patient's skin can include a fluid container, such as an intravenous bag or bags hung from an intravenous stand. The fluid container includes a first fluid compartment and a second fluid compartment, or the two fluids could be held in separate containers. In some embodiments, a first fluid, such as zinc chloride ($ZnCl_2$), is retained in the first fluid compartment and a second fluid, such as sodium chlorite ($NaClO_2$), a source of chlorite ions, is retained in the second fluid compartment. Before irrigating the patient's skin, a portion of the first fluid and a portion of the second fluid is released from the first fluid compartment and the second fluid compartment, respectively, into a fluid charging portion. The portion of the first fluid and the portion of the second fluid mix and/or interact in the fluid charging portion to form a charged compound. For example, a portion of the $ZnCl_2$ interacts with a portion of the $NaClO_2$ to form a charged zinc compound having free available zinc ions and at least one $E_h$ raising component (e.g., the $NaClO_2$ acts like an $E_h$ raising component with the chlorite ions and when interacting with the $ZnCl_2$). By providing the charged compound to a wound area, the free available zinc ions and the at least one $E_h$ raising component has been shown to prevent lowering of the $E_h$ levels in the wound area, thereby inhibiting metabolism and/or growth of bacteria, which may prevent and/or cure infections in the wound area.

Although sodium chlorite is referred to herein, it should be understood that other redox potential-raising compounds as a source of stable chlorite, such as oxychlorides, which can be prevented from degrading to chlorine dioxide, are contemplated by the present disclosure, and the embodiments with sodium chlorite are described as examples. The chlorine dioxide of the $NaClO_2$ (sodium chlorite) has antimicrobial properties and has been used for disinfection and control of bacterial fouling, as well as controlling taste, odor, and oxidation of metal ions. Using sodium chlorite as a redox potential-raising compound rather than as a source of chlorine dioxide is very important, because chlorine dioxide at elevated levels may combine with amino acids to produce potentially mutagenic compounds. Chlorine dioxide is made available at lower, controlled levels by maintaining a neutral or basic pH of the component providing $NaClO_2$, such that degradation of the sodium chlorite is avoided. Furthermore, neutral pH or basic pH provides chlorite ion stability. Additional components, such as, but not limited to, hydrogen peroxide, may be included in the charged wound irrigant to help stabilize the ions, and control pH of the separate solutions, and of the charged wound irrigant.

The charged wound irrigant may also include chlorhexidine gluconate, which is an antiseptic or disinfectant used to reduce bacteria and prevent biofilm formation. The chlorhexidine gluconate may be provided in any effective amount in the charged wound irrigant. For example, the chlorhexidine gluconate may be about 0.01% to 2% of the charged wound irrigant by volume. In an embodiment, the chlorhexidine gluconate may be about 0.05% of the charged wound irrigant by volume. The charged wound irrigant may alternatively or additionally include cetylpyridinium chloride, which is also an antiseptic used to kill bacteria and microorganisms in tissue and wounds. The chlorohexidine gluconate and/or the cetylpyridinium chloride may be included in either or both solutions prior to combining to form the charged wound irrigant, or may be included in a separate solution for adding to the charged wound irrigant. The addition of chlorhexidine gluconate and/or the cetylpyridinium chloride provide additional antimicrobial properties to the charged wound irrigant, specifically to reduce bacteria and prevent biofilm formation.

Furthermore, the charged wound irrigant may further include an antibiotic agent, antiviral agent, antifungal agent, other antimicrobial agent, or combinations thereof, in either or both solutions prior to combining to form the charged wound irrigant, or include the antibiotic agent, antiviral agent, antifungal agent, other antimicrobial agent, or combinations thereof in a separate solution for adding to the charged wound irrigant. In some embodiments, the charged wound irrigant includes one or more antibiotic agent, antiviral agent, antifungal agent, other antimicrobial agent, or combinations thereof. The antibiotic agent, antiviral agent, antifungal agent, other antimicrobial agent, or combinations thereof, may be selected per the type of wound, surgical site, infection, or tissue to be irrigated/treated. The charged wound irrigant may also include a protein such as a transforming growth factor beta (TGF-β) protein to promote wound healing. The TGF-β additive may be any of three isoforms of TGF-β (β1, β2, β3) or a combination thereof.

The solutions forming the wound irrigant may be separately stored until time for use, as the charged nature of the wound irrigant may be temporary. That is, the charged wound irrigant may lose its charge over time as the free available ions are reduced such that it may be unable to raise the redox potential of the wound site (or inhibit lowering of the redox potential). The solutions are stored separately at either neutral, acidic or basic pH, and combined at the time of use. For example, storing sodium chlorite at neutral or basic pH may prevent any significant degradation to chlorine dioxide. Storing of zinc chloride at acidic pH may help insure the availability of zinc ions. Also, an acidic pH may convert sulfur anions to the acidic forms which result in a higher $E_h$. In the case of hydrogen sulfide, because hydrogen sulfide is volatile, its formation serves as an effective means of getting rid of electrons carried by sulfide anion that are particularly conducive to lowering the $E_h$. Third, catalase degradation of hydrogen peroxide may be inhibited at an acidic pH. An acidic pH and the presence of chloride ion, ensures that the hydrogen peroxide in the composition is not degraded with storage and hence retains its effectiveness.

The charged wound irrigant may be applied by first combining two solutions retained in separate compartments in a charging portion to form the charged compound, and then distributed via an irrigation sleeve, an aerosol irrigator, or other suitable irrigator. Examples of the distribution and application system for the charged wound irrigant is provided in U.S. patent application Ser. No. 15/686,612 and U.S. patent application Ser. No. 15/686,617, which are hereby incorporated in their entirety by reference.

The wound irrigant disclosed may be used for various types of surgical sites and infections in order to increase the redox potential to decrease metabolism and growth of bacteria in the wound or tissue, and also decrease or eradicate the formation of biofilms. The wound irrigant may be applied via any mechanism appropriate for the type of wound, surgical site, or tissue. Examples of suitable dispensing mechanisms are disclosed in U.S. patent application Ser. No. 15/686,612, which is herein incorporated in its entirety. For example, the charged wound irrigant may be applied as an acne wash to skin, and include a dual-chambered container with a pump such that the 2 (or more) solutions are combined immediately before use to form the charged wound irrigant, which can then be applied by rinsing and washing the skin. As an acne wash, the charged wound irrigant may help reduce acne and prevent infection of open wounds in the skin and subdermal tissue caused by acne. For example, an aerosolized wound irrigant may be used for certain pulmonary applications, such as for pneumonia (and more particularly healthcare-associated pneumonia, HCAP or nosocomial or hospital-acquired pneumonia, HAP, or ventilator-associated pneumonia, VAP), and other respiratory infections, like bronchitis. The aerosolizer for distributing the charged wound irrigant may be, but is not limited to, a nebulizer, atomizer, mister, or other aerosol dispensing device. In other examples, bladder irrigation may be used to distribute the charged wound irrigant via a catheter (e.g., an indwelling catheter, or a catheter solely for irrigation) to the bladder and/or urethra to treat and/or prevent urinary tract infections or bacterial colonization, including but not limited to catheter associated urinary tract infections (CAUTIs).

The wound irrigation system may include an irrigator. For example, the system may include an irrigation sleeve, an aerosol irrigator, or other suitable irrigator. The charged compound may be delivered to the irrigator from the fluid charging portion. The irrigator can then be used to apply the charged compound to a wound site. For example, the irrigator can be used by a medical professional to apply the charged compound to a chronically occurring wound, to an operative and/or postoperative surgical wound, to an injury wound, directly an area on the patient's skin that does not include a wound, to other suitable areas on the patient's skin, or a combination thereof. Chronically occurring wounds may include diabetes ulcers, decubitus ulcers, venous stasis ulcers, skin affected by eczema, skin affected by psoriasis, chronic skin infections, other suitable chronically occurring wounds, or a combination thereof. In some embodiments, the charged compound may be applied to non-chronically occurring wounds, such as, skin affected by contact with poison ivy, poison oak, skin affected by other skin irritants, skin affected by allergic reactions, or other suitable non-chronically occurring wounds, or a combination thereof.

In some embodiments, the system is adapted to prevent irrigation of the patient's skin and/or wound area when the charged compound is not charged. For example, after a period of time, the charged compound may lose its charge, such that, an amount of free available zinc ions in the charged compound may be reduced, which may render the charged compound ineffective for eradicating bacteria or other pathogens or preventing the lowering of $E_h$ in a wound area. In other embodiments, the charged fluid is kept on the wound site even after losing its charge to further provide antibiotics, antiseptics, vitamins, or protein to the wound. In at least one embodiment, keeping the fluid on the wound site may continue to prevent lowering of the $E_h$ of the wound area even after losing its charge.

In some embodiments, the system may include a valve disposed at or near the fluid charging portion. The valve may be manually or automatically controlled and may control flow of the charged compound to the irrigator. For example, a medical professional operating the system may open the valve to release the charged compound from the fluid charging portion. The medical professional may then close the valve after a predetermined time and/or after a predetermined amount of the charged compound has been released from the fluid charging portion. The predetermined amount of time and/or the predetermined amount of charged compound may correspond to an amount of charged compound that the irrigator can apply to the wound area and/or the patient's skin before the charged compound loses its charge.

In some embodiments, the system may include a timer, such as a stopwatch, a counter, a clock, or other suitable timer. The timer may be disposed on a portion of the system that is readily visible to the medical professional operating the system. For example, the time may be disposed at or near the container, at or near the irrigator, or other suitable position on the system. The timer may act as a visual guide for the operator to determine when the charged compound has lost or started to lose its charge. The medical professional may stop irrigating the wound area and/or patient's skin based on the time. In some embodiments, the time may include a countdown time. For example, the timer may be started when charged compound is released from the fluid charging portion. The timer may be set to an amount of time that the charged compound will retain enough free available zinc ions to effectively increase $E_h$ in the wound area. The medical professional may stop irrigating the wound area and/or patient's skin when the timer reaches zero. In other embodiments, the charged fluid is kept on the wound site for a prolonged period of time, regardless of whether the fluid is charged, to continuously impart antimicrobial, antibiotic, or antiseptic effects on the wound site, or continue to prevent the lowering of the oxidation-reduction potential of the wound site, thus reducing risk of infection even after the medical professional has finished irrigating.

Figure 2:
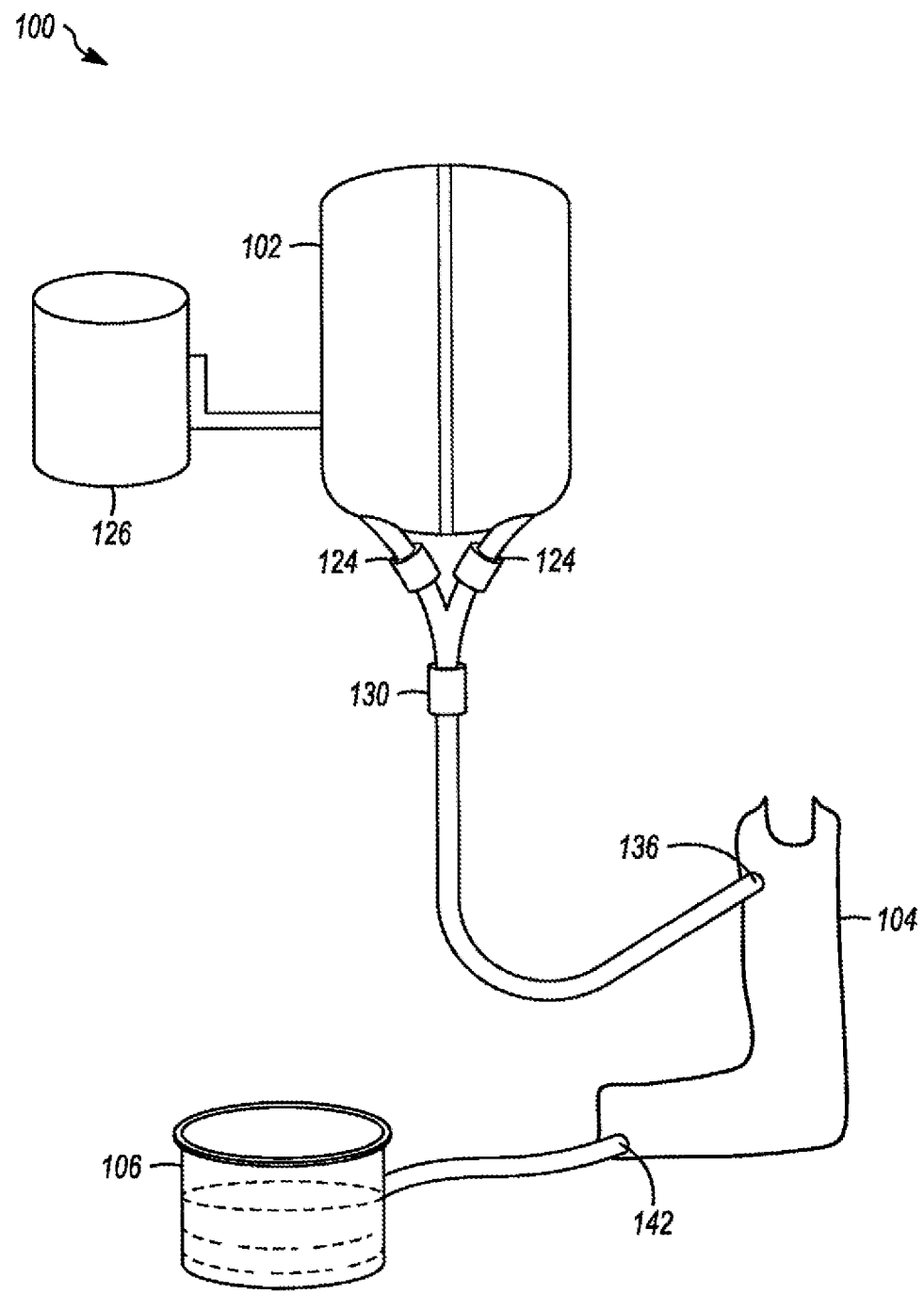

FIGS. 1 and 2 generally illustrate a patient wound and/or skin irrigation system 100, according to the principles of the present disclosure. The system includes a container 102, an irrigator or irrigation sleeve 104, and a reservoir 106. In some embodiments, the container 102 includes an intravenous bag, a canister having cylindrical profile or other suitable profile, or other suitable container. The container 102 is adapted to receive one or more fluids. For example, the container 102 includes a first or upper portion 108. The upper portion 108 may include an opening and/or a port adapted to receive the one or more fluids. In some embodiments, the upper portion 108 includes a plurality of openings and/or ports adapted to receive fluid.

In some embodiments, the container 102 includes at least one divider 110. The divider 110 is disposed in an inner portion of the container 102 and is adapted to divide the container 102 into a first compartment 112 disposed on a first side of the divider 110 and a second compartment 114 disposed on a second side of the divider 110 that is opposite the first side of the divider 110. While only a divider 110 is described herein, the principles of the present disclosure apply to a container 102 having any suitable number of dividers 110. Further, the principles of the present disclosure apply to a container 102 having additional or fewer compartments than described herein. The divider 110 is adapted to isolate fluid in the first compartment 112 from fluid in the second compartment 114, such that, the fluid in the first compartment 112 does not mix and/or interact with the fluid in the second compartment 114.

In some embodiments, the first compartment 112 is adapted to retain a first fluid. For example, as described above, the container 102 includes one or more openings and/or ports adapted to receive one or more fluids. In some embodiments, a first opening and/or port may correspond to the first compartment 112. For example, the first opening and/or port is adapted to receive the first fluid and direct the first fluid to the first compartment 112. The second compartment 114 is adapted to retain a second fluid. For example, a second opening and/or port may correspond to the second compartment 114. For example, the second opening and/or port is adapted to receive the second fluid and direct the second fluid to the second compartment 114.

In some embodiments, the first fluid is a different fluid from the second fluid. The first fluid includes a fluid capable of chemically interacting with the second fluid to form a charged compound. For example, the first fluid includes zinc chloride ($ZnCl_2$) and the second fluid includes sodium chlorite ($NaClO_2$). It should be understood that the first fluid and the second fluid are interchangeable. For example, the first fluid may include sodium chlorite and the second fluid may include zinc chloride. In some embodiments, the first fluid includes dichlorosilver ($AgCl_2$) and the second fluid includes sodium chlorite ($NaClO_2$). In some embodiments, the first fluid includes silver nitrate ($AgNO_3$) and the second fluid includes normal saline solution. In some embodiments, the first fluid includes copper chloride ($CuCl_2$) and the second fluid includes sodium chlorite ($NaClO_2$). Additionally, or alternatively, the container 102 may include one or more additional fluid compartments. The one or more additional fluid compartments may be adapted to retain one or more additional fluids. For example, the one or more additional fluids may include antibacterial fluids (e.g., cetylpyridinium chloride, chlorhexidine gluconate, or other antiseptics), vitamin fluids, other suitable fluids, or a combination thereof. In some embodiments, the vitamin fluids may include vitamin A fluid, vitamin C fluid, vitamin D fluid, vitamin E fluid, other suitable vitamin fluids, or a combination thereof. In some embodiments, the first fluid and/or the second fluid may be infused with one or more antibiotics, one or more vitamins, or a combination thereof.

In an embodiment, the wound irrigant may include a Vitamin C component. The Vitamin C may be any form of Vitamin C such as, but not limited to, ascorbic acid, ascorbates such as mineral ascorbates, flavonoids, or mixtures or variations thereof having antioxidant properties. The Vitamin C component may have wound healing properties in addition to the antioxidant properties. In some instances, the Vitamin C component may have antimicrobial properties. The Vitamin C component may be included in either or both solutions prior to charging, or be included in a separate solution to be combined with the charged irrigant. The Vitamin C component may be included in any effective concentration, as determined by the type of Vitamin C component and the solutions provided. For example, the Vitamin C component may be about 1 mM to 10 mM, about 2 to 8 mM, or about 3 to 7 mM concentration of an ionically charged zinc solution. In an embodiment, the Vitamin C component is about 1 mM of the wound irrigant. In another example, for graft healing, the Vitamin C component may be included at about 3 mg/ml of wound irrigant. Additionally, in some embodiments, the charged wound irrigant may further include other vitamins, including, but not limited to, Vitamin A, Vitamin D, Vitamin E, Vitamin $B_{1-6}$, Vitamin $B_{12}$, and others and mixtures thereof. For example, B Vitamins may provide prophylactic properties against potential host tissue toxicity and/or oxidative damage of components in the wound irrigant.

In an embodiment, the charged wound irrigant may be used in skin graft applications to help prevent/fight infection, reduce host rejection, and promote growth. As such, an ionically charged zinc solution including a Vitamin C component, chlorhexidine gluconate/cetylpyridinium chloride, and optionally an antibiotic, may be sprayed or misted onto the skin graft site twice daily, for example, based on the effective amounts of the zinc ions, Vitamin C component, antiseptic, and/or antibiotic.

In another embodiment, the charged wound irrigant may be used to provide an antimicrobial effect in burn wound applications to promote skin healing/re-epithelialization and prevent/fight infections. The Vitamin C component may provide anti-oxidant properties, as well as an anti-inflammatory effect to decrease pain and swelling at the burn site.

In yet another embodiment, the charged wound irrigant may be used to irrigate an open wound for surgical preparation. Open wounds cannot be prepared using toxic irrigants such as iodine, chlorhexidine, alcohol, and $H_2O_2$. The charged wound irrigant may be supplied via a prep-stick, which is cracked to combine the solutions prior to application to the open wound site. By cracking the separator between the two solutions, the solutions can be mixed to form the ionically charged composition. The charged wound irrigant may confer a long-lasting antibacterial effect that would endure the length of the surgery and beyond based on the effective amounts of redox potential raising components, inhibiting bacterial recolonization of the skin or surrounding tissue.

A ratio of the first fluid to the second fluid may vary based on the application and/or use of resulting charged compound and/or various characteristics of the first fluid and the second fluid may be altered and/or controlled, such that, a desired charged compound results from the interaction between the first fluid and the second fluid. Such ratios and/or characteristics are described in U.S. Pat. No. 6,409,992, which is incorporated by reference herein.

As described above, when the first fluid and the second fluid form a charged compound when the first fluid and the second fluid interact with one another. The system 100 includes a fluid charging portion 118. The fluid charging portion 118 is disposed at or near a lower portion 120 of the container 102. The second or lower portion 120 is disposed on an opposite side of the container 102 from the upper portion 108.

In some embodiments, one or more fluid transfer portions 122 extend from the lower portion 120 to the fluid charging portion 118. For example, a first fluid transfer portion 122A extends from the lower portion 120 to the fluid charging portion 118 and a second fluid transfer portion 122B extends from the lower portion 120 to the fluid charging portion 118. The first fluid transfer portion 122A is in communication with the first compartment 112 and the second fluid transfer portion 122B is in communication with the second compartment 114. While only a first and second transfer portions 122A and 122B are described herein, the system 100 may include any suitable number of transfer portions 122 in communication with corresponding compartments of the container 102.

In some embodiments, a portion of the first fluid transfers from the first compartment 112 to the fluid charging portion 118 via the first fluid transfer portion 122A and a portion of the second fluid transfers from the second compartment 114 to the fluid charging portion 118 via the second fluid transfer portion 122B. For example, each fluid transfer portion 122 may include a valve 124, as is generally illustrated in FIG. 2. The valves 124 are adapted to release fluid from the container 102 into the fluid charging portion 118. For example, each valve 124 may include a shutoff valve that is selectively opened to allow fluid to transfer from the container 102 to the fluid charging portion 118. In some embodiments, a medical professional operating the system 100 may actuate a control, such as a lever or a knob, associated with a valve 124 in order to allow fluid to transfer from the container 102 to the fluid charging portion 118. Conversely, the medical professional may actuate the control to prevent fluid from transferring from the container 102 to the fluid charging portion 118.

In some embodiments, fluid transfers from the container 102 to the fluid charging portion 118 due to the force of gravity acting on the fluid. The container 102 may be disposed at a position above the fluid charging portion 118. For example, the container 102 may be hung on an intravenous stand or other suitable stand. In some embodiments, the medical professional may hold the container 102 above the fluid charging portion 118 in order to allow gravity to act on fluid within the container 102.

In some embodiments, a pump, such as a pump 126, as is generally illustrated in FIG. 2, may promote transfer of fluid from the container 102 to the fluid charging portion 118. For example, the pump 126 may be in communication with the container 102 or other suitable component of the system 100. The pump 126 may create a current and/or force that promotes transferring the fluid from the container 102 to the fluid charging portion 118. This force can be either in the form of positive pressure or the creation of a vacuum effect or a milking effect.

As described above, the portion of the first fluid transferred from the first compartment 112 interacts with the portion of the second fluid from the second compartment 114 to form a charged compound when the portion of the first fluid and the portion of the second fluid are in the fluid charging portion 118. In some embodiments, the charged compound transfers from the fluid charging portion 118 to a compound delivery portion 128 that extends from a first end of the compound delivery portion 128 from the fluid charging portion 118.

In some embodiments, the compound delivery portion 128 includes a flexible polymer tube or hose, a corrugated tube or hose, and/or other suitable tube or hose. The compound delivery portion 128 includes a generally circular profile having a diameter and a length. In some embodiments, the diameter and length may allow the charged compound to flow the compound delivery portion 128 at a predetermined rate. For example, a larger diameter may allow the charged compound to flow through the compound delivery portion 128 at a faster rate than a smaller diameter. Additionally, or alternatively, a longer length may allow the charged compound to flow through the compound delivery portion 128 at a slower rate than a shorter length.

In some embodiments, a control 130, as is generally illustrated in FIG. 2, may be disposed on the compound delivery portion 128 at or near the fluid charging portion 118. The control 130 may include features similar to those of the valves 124 described above. The medical professional operating the system 100 may actuate the control to allow the charged compound to transfer from the fluid charging portion 118 to the compound delivery portion 128.

In some embodiments, the charged compound is drawn into the compound delivery portion 128 as a result of the force of gravity acting on the charged compound and/or as a result of the pump 126 promoting the charged compound through the compound delivery portion 128. In some embodiments, a second end of the compound delivery portion 128 is adapted to connect to, couple to, attach to, and/or be in communication with the irrigation sleeve 104.

For example, the irrigation sleeve 104 includes a first aperture 132 disposed near an upper portion 134 of the irrigation sleeve 104. In some embodiments, the second end of the compound delivery portion 128 is adapted to be inserted into the first aperture 132. In some embodiments, the first aperture 132 may include a port adapted to receive the second end of the compound delivery portion 128. Additionally, or alternatively, the second end of the compound delivery portion 128 may be adapted to connect to, couple to, attach to, and/or be in communication with the first aperture 132 in other suitable manners than those described herein.

As described above, the charged compound transfers from the fluid charging portion 118 to the compound delivery portion 128. The charged compound exits the compound delivery portion 128 at the second end of the compound delivery portion 128 and enters the irrigation sleeve 104 at the first aperture 132. In some embodiments, and as is generally illustrated in FIG. 2, the first aperture 132 may include a filter 136. The filter 136 may include a screen or other suitable filter and is adapted to filter particulates from the charged compound before the charged compound irrigates the wound area and/or the patient's skin.

In some embodiments, the irrigation sleeve 104 contains a profile. The profile may include a profile corresponding to a portion of the patient's anatomy. For example, and as is generally illustrated in FIGS. 1 and 2, the profile may include a profile corresponding to a patient's foot. The irrigation sleeve 104 may include a generic profile, such that, the profile may accommodate various patients. In some embodiments, the profile may be adapted to match a particular patient. For example, the irrigation sleeve 104 may include a profile that corresponds to a patient's foot. The patient's foot may be measured and/or examined. The irrigation sleeve 104 may be manufactured to match the measurements and/or examination of the patient's foot.

In some embodiments, the profile may include a generic shape such as a cylinder. The irrigation sleeve 104 having a profile that includes a generic shape may be wrapped around a portion of the patient's anatomy, such as an arm or a leg. In some embodiments, the irrigation sleeve 104 may include an attachment portion (not shown). For example, a portion of the irrigation sleeve 104 may be opened to receive the corresponding portion of the patient's anatomy. The irrigation sleeve 104 may include closing mechanism adapted to close the irrigation sleeve 104 around the corresponding portion of the patient's anatomy. The closing mechanism may include a strap, tape, hook-and-loop fasteners, or other suitable closing mechanism. In some embodiments, irrigation sleeve 104 may be slid over the corresponding portion of the patient's anatomy. For example, the irrigation sleeve 104 generally illustrated in FIGS. 1 and 2 may be slid onto a patient's foot like a sock. In some embodiments, the irrigation sleeve 104 may include tightening features. For example, the irrigation sleeve 104 may include laces, straps, or other features that tighten and/or compress the irrigation sleeve 104 onto the patient.

In some embodiments, the irrigation sleeve 104 may include one or more fluid seals. The fluid seals may be disposed at one or more openings of the irrigation sleeve 104 in order to prevent fluid, such as the charged compound, from exiting the irrigation sleeve 104 at the one or more openings. In some embodiments, the irrigation sleeve 104 may include a fluid seal disposed around the upper portion 134, such that, when the irrigation sleeve 104 is on the patient, a fluid tight seal is formed at the upper portion 134.

In some embodiments, the irrigation sleeve 104 may include one or more manual or automatic pumps, which may remove the air from the sleeve, decreasing the potential space. This allows the use of smaller amount of fluid to envelop the anatomy of concern and engage the desired surfaces.

In some embodiments, the irrigation sleeve 104 covers one or more wound areas on the patient. By way of non-limiting example only, the irrigation sleeve 104 may be adapted to cover one or more diabetic foot ulcers. While only limited examples are described herein, the irrigation sleeve 104 may be adapted to cover any suitable wound area or portion of the patient's skin. As the charged compound enters the irrigation sleeve 104 through the first aperture 132, the charged compound is directed to the one or more wound areas. The charged compound irrigates the one or more wound areas and/or the patient's skin in order to promote higher levels of $E_h$ in the one or more wound areas, which decreases metabolism and/or growth of anaerobic bacteria in the one or more wound areas. By decreasing metabolism and/or growth of bacteria in the one or more wound areas, infections in the one or more wound areas may be prevented and/or cured. Colonization may also be decreased, thereby increasing the wound healing potential in the area.

As described above, the charge of the charged compound decreases over a period. As the charge of the charged compound decreases below a charge threshold, the charged compound is converted into a residual compound. The residual compound may be ineffective over time to promote higher levels of $E_h$ in the one or more wound areas. In order to prevent the residual compound from irrigating the one or more wound areas, the control 130 may include a timer. The timer may act as a visual guide for the medical professional to determine when the charged compound has lost or started to lose its charge. The medical professional may stop irrigating the wound area and/or patient's skin based on the timer. In some embodiments, the timer may include a countdown time. For example, the timer may be started when charged compound is released from the fluid charging portion 118. The timer may be set to an amount of time that the charged compound will retain enough free available ions to maintain antimicrobial efficacy or effectively increase $E_h$ in the one or more wound areas. The medical professional may stop irrigating the one or more wound areas and/or patient's skin when the timer reaches zero. While only limited examples are described herein, the timer may include any suitable timer.

In some embodiments, the residual compound may be released from the irrigation sleeve 104. In some embodiments, the irrigation sleeve 104 includes a second aperture 138. The second aperture 138 may be disposed at a lower portion 140 of the irrigation sleeve 104. The lower portion 140 is disposed on the irrigation sleeve 104 opposite the upper portion 134. In some embodiments, a valve may be disposed at or near the second aperture 138. The medical professional may actuate the valve to create a vacuum effect within the irrigation sleeve 104. The vacuum effect may act to draw the residual compound toward the second aperture 138. In some embodiments, the force of gravity acting on the residual compound may act to draw the residual compound toward the second aperture 138. The residual compound may exit the irrigation sleeve 104 through the second aperture 138. In some embodiments, a filter 142 may be disposed at or near the second aperture 138. The filter 142 includes features similar to the filter 136.

In some embodiments, a drain portion 144 is connected to, coupled to, attached to, or in communication with the second aperture 138 at a first end of the drain portion 144. The drain portion 144 may include a tube or hose and includes features similar to those of the compound delivery portion 128. The drain portion 144 extends from the second aperture 138 from the first end of the drain portion 144 to a second end of the drain portion 144. The second end of the drain portion 144 may be connected to, coupled to, attached to, or in communication with the reservoir 106.

The reservoir 106 may include canister having a generally cylindrical profile. In some embodiments, the reservoir 106 may include a canister having a profile other than cylindrical, a bag, a receptacle, or other suitable reservoir. The reservoir 106 is adapted to receive the residual compound through the drain portion 144. In some embodiments, the reservoir 106 may receive residual compound from a plurality of irrigation sleeves 104. The residual compound with in the reservoir 106 may be disposed of after the residual compound is received by the reservoir 106.

Figure 3:
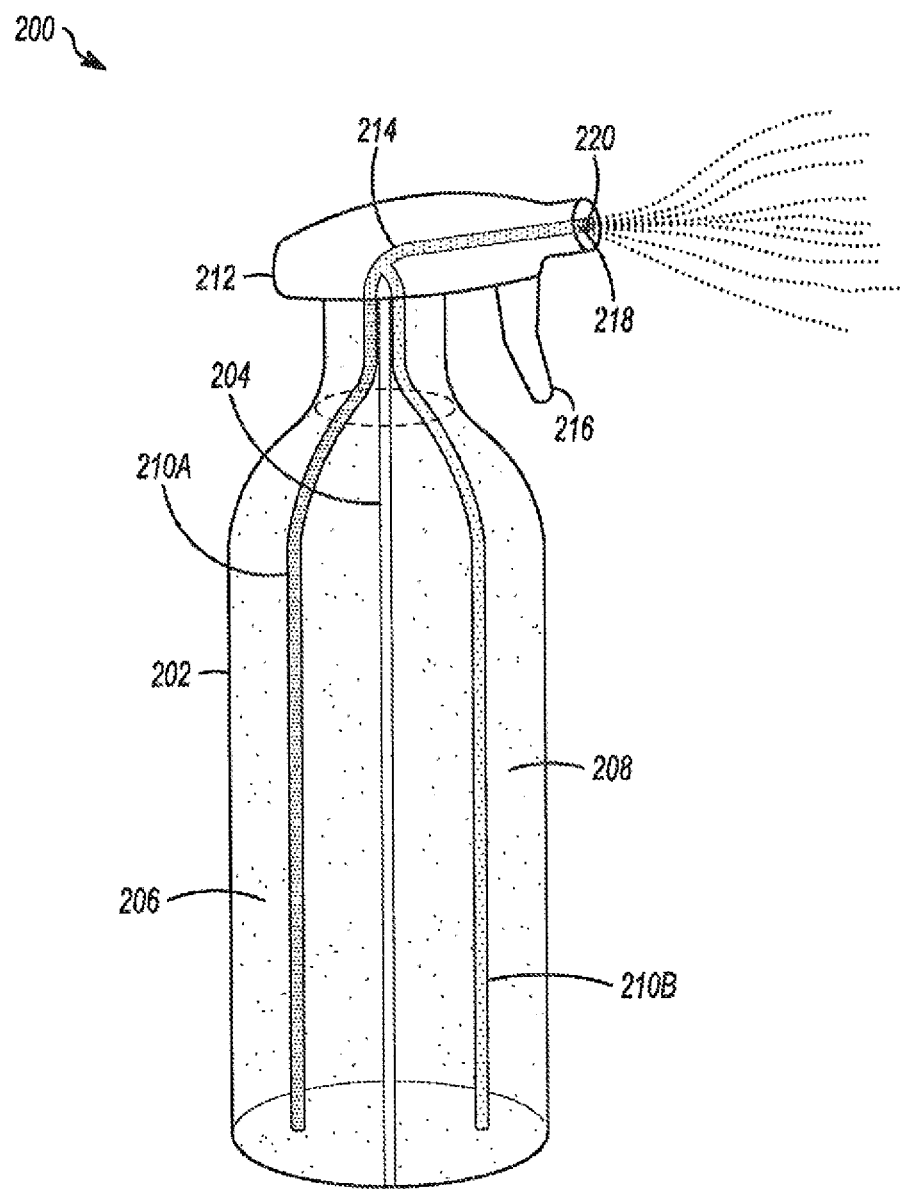
FIG. 3 generally illustrates an alternative wound and/or skin irrigation system according to the principles of the present disclosure.

FIG. 3 generally illustrates an alternative wound and/or skin irrigation system 200 according to the principles of the present disclosure. In some embodiments, a medical professional may irrigate surgical wounds during (operative wounds) and/or after (postoperative wounds) a patient surgery. The medical professional may operate the system 200 to direct charged compound to the operative and/or postoperative wounds to raise $E_h$ in the wounds in order to prevent and/or cure operative and/or postoperative infections in the wounds. The system 200 may include a portable or substantially portable irrigation system that includes a container 202. The container 202 may include a generally cylindrical profile or other suitable profile. The container 202 is adapted to receive one or more fluids and includes features similar to those of the container 102. In some embodiments, the container 202 includes a divider 204. The divider 204 includes features similar to the divider 110. The divider 204 defines a first compartment 206 disposed on a first side of the divider 204 and a second compartment 208 disposed on a second side of the divider 204. The second side of the divider 204 is disposed opposite the first side of the divider 204.

The first compartment 206 includes features similar to those of the first compartment 112 and the second compartment 208 includes features similar to those of the second compartment 114. The first compartment 206 is adapted to receive and retain a first fluid. The first fluid includes features similar to the first fluid described above with respect to FIGS. 1 and 2. The second compartment 208 is adapted to receive and retain a second fluid. The second fluid includes features similar to the second fluid described above with the respect to FIGS. 1 and 2. While only a first compartment 206 and a second compartment 208 is described herein, the system 200 may include any suitable number of compartments and may receive and retain any suitable number of fluids.

The system 200 includes one or more fluid transfer portion 210. For example, the system 200 includes a first fluid transfer portion 210A disposed in the first compartment 206 and a second fluid transfer portion 210B disposed in the second compartment 208. The first fluid transfer portion 210A is adapted to allow a portion of the first fluid to be drawn out of the first compartment 206 and the second fluid transfer portion 210B is adapted to allow a portion of the second fluid to be drawn out of the second compartment 208.

In some embodiments, the system 200 includes an irrigator 212 disposed at or near an upper portion of the container 202. The irrigator 212 is adapted to apply charged compound to a surgical wound. For example, the irrigator 212 includes a fluid charging portion 214 disposed in an interior portion of the irrigator 212. The fluid charging portion 214 includes features similar to the fluid charging portion 118. The fluid charging portion 214 is adapted to receive the portion of the first fluid and the portion of the second fluid. As described above with respect to the fluid charging portion 118, the portion of the first fluid and the portion of the second fluid interact to form a charged compound in the fluid charging portion 214.

In some embodiments, the irrigator 212 includes an actuator 216. The actuator 216 may include a trigger or other suitable actuator. When the medical professional actuates the actuator 216, a vacuum and/or suction effect is created within the container 202. The portion of the first fluid and the portion of the second fluid are drawn into the fluid charging portion 214 in response to the vacuum and/or suction effect.

The irrigator 212 includes a compound applicator 218. The compound applicator 218 is adapted to apply the charged compound to the surgical wound by expelling the charged compound from the fluid charging portion 214 in response to the vacuum and/or suction effect created by the actuator 216. The compound applicator 218 may include a selectively adjustable head 220. The head 220 may be adjusted to provide a wider or narrower compound application field. The medical professional may direct the charged compound to the surgical wound by aiming the irrigator 212 in a direction that applies the charged compound to the surgical wound when the actuator 216 is actuated by the medical professional.

Figure 4:
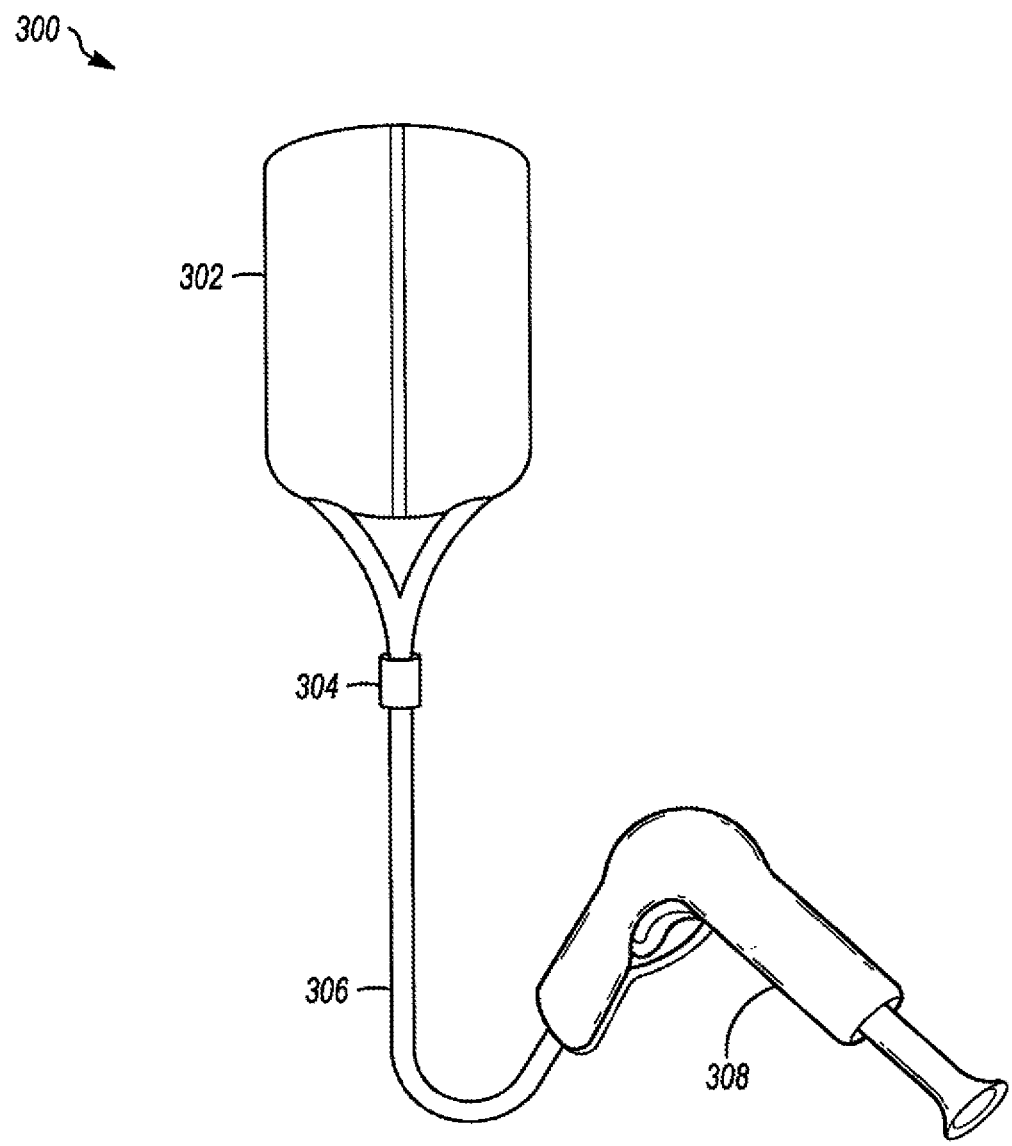
FIG. 4 generally illustrates an alternative wound and/or skin irrigation system according to the principles of the present disclosure.

FIG. 4 generally illustrates an alternative wound and/or skin irrigation system 300 according to the principles of the present disclosure. The medical professional may operate the system 300 to direct charged compound to the operative and/or postoperative wounds to raise $E_h$ in the wounds in order to prevent and/or cure operative and/or postoperative infections in the wounds. The system 300 may include a portable or substantially portable irrigation system that includes a container 302. The container 302 includes features similar to those of the container 102 described with respect to FIGS. 1 and 2. The system 300 includes a fluid charging portion 304. The fluid charging portion 304 includes features similar to those of the fluid charging portion 118 described with respect to FIGS. 1 and 2. The system includes a compound delivery portion 306. The compound delivery portion 306 includes features similar to those the compound delivery portion 128 described with respect to FIGS. 1 and 2.

In some embodiments, the system 300 includes an irrigator 308. The irrigator 308 may include features similar to those of the irrigator 212 described with respect to FIG. 3. In some embodiments, the irrigator 308 includes a continuously or substantially continuously irrigating irrigator. For example, the irrigator 308 may include a powered and/or motorized irrigator adapted to continuously or substantially continuously apply charged compound to a surgical wound. The medical professional may actuate an actuator associated with the irrigator 308. While the actuator is actuated, the irrigator 308 may continuously or substantially continuously apply charged compound to a surgical wound that the medical professional is aiming and/or directing the irrigator 308 toward.

Figure 5:
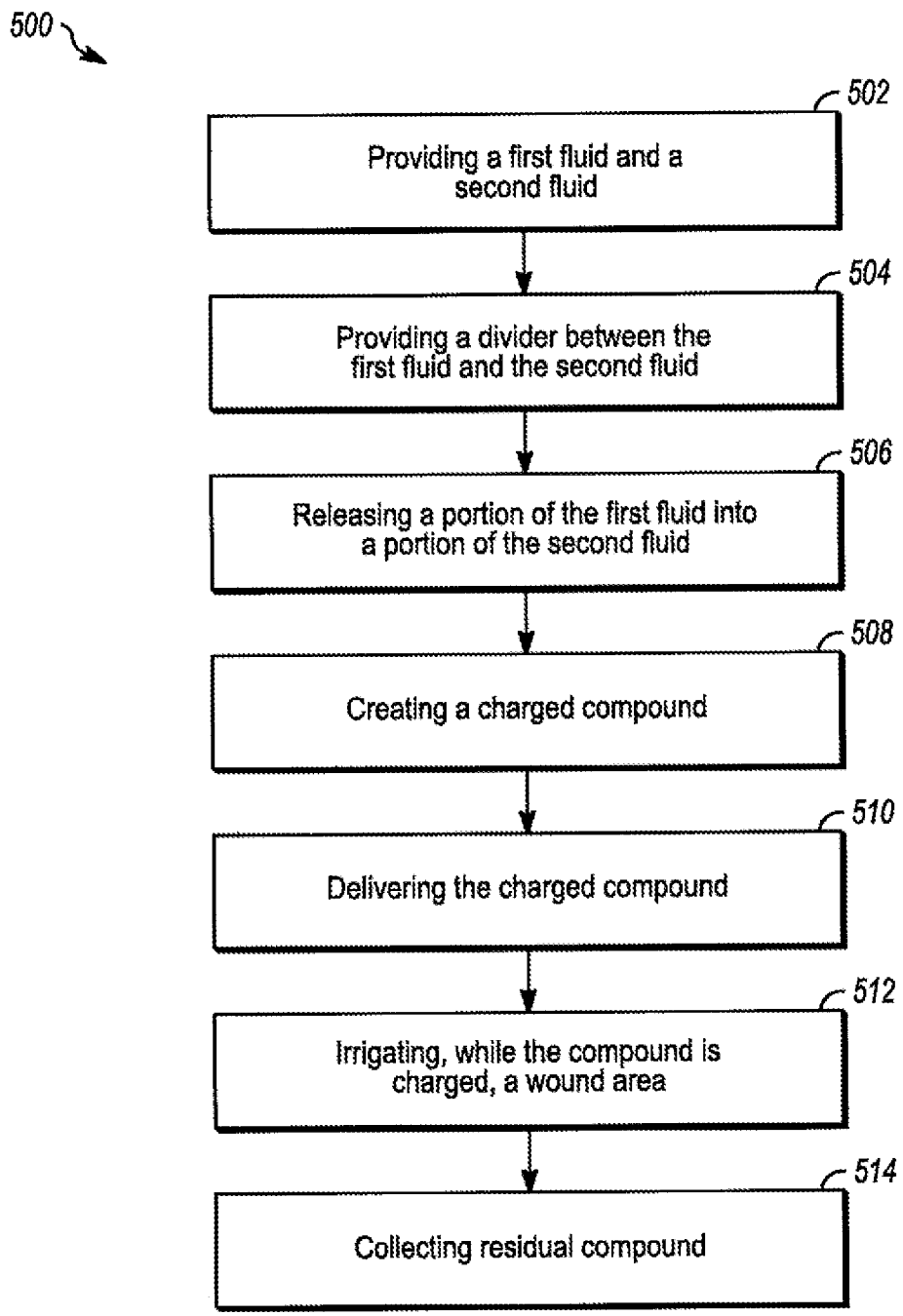
FIG. 5 is a flow diagram illustrating a wound and/or skin irrigation method according to the principles of the present disclosure.

FIG. 5 is a flowchart generally illustrating a wound and/or skin irrigation method 500 according to the principles of the present disclosure. At 502, the method 500 includes providing a first fluid and a second fluid. For example, as described above, the first fluid and the second fluid may be provided in a first compartment and a second compartment respectively. At 504, the method 500 includes providing a divider between the first fluid and the second fluid. For example, the divider may be provided to separate the first fluid from the second fluid, such that, the first fluid does not interact with the second fluid.

At 506, the method 500 includes releasing a portion of the first fluid and a portion of the second fluid. For example, the portion of the first fluid and the portion of the second fluid may be released to a fluid charging portion, such as the fluid charging portion 118, the fluid charging portion 214, or the fluid charging portion 304. At 508, the method 500 includes creating a charged compound. For example, the portion of the first fluid interacts with the portion of the second fluid to form a charged compound, as described above. At 510, the method 500 includes delivering the charged compound. For example, as described above, the charged compound may be delivered to the irrigation sleeve 104, the irrigator 212, or the irrigator 308.

At 512, the method 500 includes irrigating, while the compound is charged, a wound area. For example, as described above, a medical professional irrigates one or more wound areas, one or more operative and/or postoperative wounds, a portion of a patient's skin, or a combination thereof using the charged compound while the charged compound is charged. At 514, the method 500 collects residual compound. For example, as described above, as the charge of the charged compound decreases below the charge threshold, the charge compound becomes a residual compound. The residual compound may be collected by the reservoir 106. In some embodiments, the method 500 may omit 514.

The present disclosure relates to a charged wound irrigant including an ionically or electronically charged solution including a charged ion or electron (e.g., $Zn^{2+}$, $Ag^+$, $Ag^{2+}$, $Cu^{2+}$, etc.) and a Vitamin C component. The charged wound irrigant may further include chlorhexidine gluconate, cetylpyridinium chloride, an antibiotic, and/or combinations thereof. The charged ion or electron may be provided by combining solutions such as, for example, $ZnCl_2$ and $NaClO_2$. The charged wound irrigant increases the redox potential at the wound site, thus reducing bacterial proliferation and preventing/curing/fighting infections of wounds, surgical sites, bodily fluids, joints, peritoneum, organs, body cavities, abscesses, and tissue, around implanted non-biologic materials such as joint prostheses, hernia mesh, trauma hardware, spine instrumentation, stimulator devices, defibrillators, pacemakers, breast implants, etc. As noted above, the charged wound irrigant may be used to treat surgical sites, wounds, or infections in or on human bodies, as well as in or on animal bodies in the veterinary setting, as animals are subject to similar infection risks from open wounds and surgeries.

As used herein, the terminology "or" is intended to mean an inclusive "or" rather than an exclusive "or". That is, unless specified otherwise, or clear from context, "X includes A or B" is intended to indicate any of the natural inclusive permutations. That is, if X includes A; X includes B; or X includes both A and B, then "X includes A or B" is satisfied under any of the foregoing instances. In addition, the articles "a" and "an" as used in this application and the appended claims should generally be construed to mean "one or more" unless specified otherwise or clear from context to be directed to a singular form.

Further, for simplicity of explanation, although the figures and descriptions herein may include sequences or series of steps or stages, elements of the methods disclosed herein may occur in various orders or concurrently. Additionally, elements of the methods disclosed herein may occur with other elements not explicitly presented and described herein. Furthermore, not all elements of the methods described herein may be required to implement a method in accordance with this disclosure. Although aspects, features, and elements are described herein in particular combinations, each aspect, feature, or element may be used independently or in various combinations with or without other aspects, features, and elements.

While the disclosure has been described in connection with certain embodiments, it is to be understood that the disclosure is not to be limited to the disclosed embodiments but, on the contrary, is intended to cover various modifications and equivalent arrangements included within the scope of the appended claims, which scope is to be accorded the broadest interpretation so as to encompass all such modifications and equivalent structures as is permitted under the law.

What is claimed is:

1. A method for irrigating a wound, the method comprising:
   keeping a first fluid separate from a second fluid in a container, the first fluid including an ion rich compound having free available ions, and the second fluid including an oxidation-reduction potential increasing compound;
   keeping a third fluid having antiseptic and/or antibiotic properties separate from the first and second fluids,
   mixing the first fluid with the second fluid and mixing the third fluid with the mixture of the first and second fluids in a fluid charging portion of the container to form an ionically charged fluid; and
   applying the ionically charged fluid to the wound to increase antimicrobial activity at the wound.

2. A wound irrigation system comprising:
   a first fluid including an ion rich compound having free available ions,
   a second fluid including an oxidation-reduction potential increasing compound, the second fluid housed separately from the first fluid,
   a third fluid including an antiseptic compound, antibiotic compound, a vitamin-rich compound, a protein, or a mixture thereof, the third fluid housed separately from the first and second fluids,
   wherein mixing the first, second, and third fluids in a charging area forms an ionically charged fluid with an oxidation-reduction potential higher than a wound site oxidation-potential, and wherein the ionically charged fluid increases the wound site oxidation-potential upon application.

3. The method of claim 1, wherein the first fluid includes a source of zinc ions, silver ions, copper ions, or a mixture thereof.

4. The method of claim 1, wherein the antiseptic includes chlorhexidine gluconate, cetylpyridinium chloride, or a mixture thereof.

5. The method of claim 1, wherein applying the ionically charged fluid includes delivering the ionically charged fluid to the wound via an irrigator sleeve configured to at least partially enclose the wound.

6. The method of claim 1, wherein mixing the first fluid and the second fluid includes actuating a release to combine the first and second fluids in the fluid charging portion.

7. The method of claim 6, wherein actuating the release includes creating a vacuum in the container to draw the first and second fluids into the fluid charging portion.

8. The wound irrigation system of claim 2, wherein the first fluid includes a source of zinc ions, copper ions, silver ions, or a mixture thereof.

9. The wound irrigation system of claim 2, wherein the second fluid includes a source of chlorite ions.

10. The wound irrigation system of claim 2, wherein the antiseptic compound includes chlorhexidine gluconate, cetylpyridinium chloride, or a mixture thereof.

11. The wound irrigation system of claim 2, wherein the vitamin-rich compound includes Vitamin A, Vitamin C, Vitamin D, Vitamin E, Vitamin $B_{1-6}$, Vitamin $B_{12}$, or mixtures thereof.

12. The method for irrigating a wound of claim 1, wherein the second fluid includes a source of chlorite ions.

13. The method for irrigating a wound of claim 1, wherein the first fluid includes zinc chloride ($ZnCl_2$), dichlorosilver ($AgCl_2$) or copper chloride ($CuCl_2$).

14. The method for irrigating a wound of claim 1, wherein the protein includes a transforming growth factor beta TGF-β including β1, β2, β3, or a combination thereof).

15. The wound irrigation system of claim 2, wherein the first fluid includes zinc chloride ($ZnCl_2$), dichlorosilver ($AgCl_2$) or copper chloride ($CuCl_2$).

16. The wound irrigation system of claim 2, wherein the second fluid includes sodium chlorite ($NaClO_2$).

17. The wound irrigation system of claim 2, wherein the protein includes a transforming growth factor beta TGF-β including β1, β2, β3, or a combination thereof.

18. The would irrigation system of claim 2 further including an irrigation sleeve.

19. The would irrigation system of claim 2, wherein the system is portable.

20. The would irrigation system of claim 2 further comprising a container having a plurality of compartments and dividers structured to receive and retain the first, second, and third fluids.

* * * * *